US011318146B2

(12) United States Patent
Morrissette

(10) Patent No.: US 11,318,146 B2
(45) Date of Patent: May 3, 2022

(54) DIETARY SUPPLEMENT

(71) Applicant: James Peter Morrissette, Fort Myers, FL (US)

(72) Inventor: James Peter Morrissette, Fort Myers, FL (US)

( * ) Notice: Subject to any disclaimer, the term of this patent is extended or adjusted under 35 U.S.C. 154(b) by 280 days.

(21) Appl. No.: 16/842,705

(22) Filed: Apr. 7, 2020

(65) Prior Publication Data
US 2020/0230151 A1 Jul. 23, 2020

Related U.S. Application Data

(63) Continuation of application No. 15/672,013, filed on Aug. 8, 2017, now Pat. No. 10,624,902.

(51) Int. Cl.
*A61K 31/554* (2006.01)
*A61K 36/185* (2006.01)
*A61K 9/48* (2006.01)

(52) U.S. Cl.
CPC .......... *A61K 31/554* (2013.01); *A61K 9/4841* (2013.01); *A61K 36/185* (2013.01)

(58) Field of Classification Search
CPC .. A61K 31/554; A61K 36/185; A61K 9/4808; A61K 9/4841
See application file for complete search history.

(56) References Cited

U.S. PATENT DOCUMENTS

| 3,758,528 A | 9/1973 | Malen et al. |
| 8,198,268 B2 | 6/2012 | Guzman et al. |
| 8,367,656 B2 | 2/2013 | Sansone |
| 2008/0213401 A1 | 9/2008 | Smith |

FOREIGN PATENT DOCUMENTS

EP 2561864 A1 2/2013

OTHER PUBLICATIONS

Trademark Electronic Search System (TESS), Wordmark Search Records of "TIANAA" and "ZAZA", retrieved Mar. 24, 2022, 8 pages. (Year: 2022).*
WZDX News "Tianeptine, sold as 'Tiana,' 'Zaza Red' and 'Tiana Red' classified as Schedule II Controlled Substance", Mar. 18, 2021 (updated Jan. 26, 2022; online, URL <rocketcitynow.com/article/news/local/adph-tianeptine-schedule-ii-drug-zaza-red/525-0ecdbc1b-365f-4967-8f7d-2a20be9cd7cf>), 3 pages. (Year: 2022).*
U.S. Appl. No. 16/812,688, filed Mar. 9, 2020.
U.S. Appl. No. 16/823,975, filed Mar. 19, 2020.
U.S. Appl. No. 16/834,374, filed Mar. 30, 2020.
U.S. Appl. No. 16/842,702, filed Apr. 7, 2020.
U.S. Appl. No. 16/842,705, filed Apr. 7, 2020.
U.S. Appl. No. 16/846,216, filed Apr. 10, 2020.
U.S. Appl. No. 16/846,221, filed Apr. 10, 2020.
U.S. Appl. No. 16/846,222, filed Apr. 10, 2020.
U.S. Appl. No. 16/852,393, filed Apr. 17, 2020.
U.S. Appl. No. 16/852,396, filed Apr. 17, 2020.
Answer and Counterclaims; *Karmagreen, LLC* v. *MRSS Inc*, United States District Court Northern District of Georgia, Atlanta Division, Case No. 1:21-cv-00674-WMR; Mar. 11, 2021.
Defendant MRSS Inc.'s Initial Invalidity Contentions, *Karmagreen, LLC* v. *MRSS Inc*, United States District Court Northern District of Georgia, Atlanta Division, Case No. 1:21-cv-00674-WMR; Jun. 11, 2021.
Unknown Author, "Tianeptine," Apr. 26, 2016, https://www.drugs.com/international/tianeptine.html.
Unknown Author, "The Merck Index Online—Tianeptine," Unknown Date, https://www.rsc.org/Merck-Index/monograph/print/m10845/tianeptine.
Osonwa, et al., "Physico-Technical Properties of Tablets Formulated with Ethanolic Extract of Fresh Leaves of Combretum Micranthum G. Don," Jan. 2013, Journal of Applied Pharmaceutical Science.
Unknown Author, "Herbs of the Gods—Sakae Naa (Combretum quadrangulare) extract 25x," May 18, 2016, https://herbsofthegods.nl/sakae-naa-combretum-quadrangulare-extract-25x/.
Ali et al, "ASEAN Herbal and Medicinal Plants," Jul. 2010, The Association of Southeast Asian Nations.
Unknown Author, "Combretun Quadrangulare (Sakea Naa) Powder," Jul. 2017, worldseedsupply.com.
ZoltanBuchan, "Drugs-Forum—Combretum (Combretum quadrangulare) Possible Kratom substitute," May 7, 2012, https://drugs-forum.com/threads/combretum-combretum-quadrangulare-possible-kratom-substitute.184519/.
Saraland et al., "Medicinal Plants in Thailand, vol. 1," 1996, Bangkok.
Unknown Author, "The Merck Index," 2013, The Royal Society of Chemistry.
Unknown Author, "Calcium Silicate," Jul. 17, 2017, https://www.drugs.com/inactive/calcium-silicate-13.html.
Troy et al., "Remington: The Science and Practice of Pharmacy," 2006, Lippincott Williams & Wilkins, United States.
SUCK_A_GERBILS_DICK, "Tianeptine Free Acid," May 31, 2015, https://www.reddit.com/r/Nootropics/comments/37yqk5/tianeptine_free_acid/.
Unknown Author, "Tianeptine + Kava," Mar. 14, 2015, https://www.reddit.com/r/Kava/comments/2z0s2s/tianeptine_kava/.
Romm et al., "Botanical Medicine for Women's Health," May 5, 2009, Churchill Livingstone.
Unknown Author, "Kava," Jul. 2017, rxlist.com/kava/supplements.htm.
Sarris et al., "The Kava Anxiety Depression Spectrum Study (KADSS): a randomized, placebo-controlled crossover trial using an aqueous extract of Piper methysticum," May 9, 2009, Psychopharmacology.
Unknown Author, "Complementary and Alternative Medicine for Mental Health," Apr. 8, 2016, Mental Health America.
Tayebati, et al., "Effect of choline-containing phospholipids on brain cholinergic transporters in the rat," Dec. 31, 2010, Journal of Neurological Sciences.
Wignall, et al., "Citicoline in Addictive Disorders: A Review of the Literature," Jul. 2014, American Journal of Drug and Alcohol Abuse.
Unknown Author, "CDP-Choline and Alpha GPC: What to Feed Your Head," Apr. 25, 2017, https://www.ilifelink.com/cdp-choline_and_alpha_gpc_what_to_feed_your_head.html.

(Continued)

*Primary Examiner* — Aaron J Kosar
(74) *Attorney, Agent, or Firm* — George F. Wallace

(57) ABSTRACT

A method of forming a dietary supplement can include steps of creating a composition of matter comprising sakae naa and kava; and providing the composition of matter in a liquid or solid form. Providing the composition of matter can include filling a container with the composition of matter.

6 Claims, 5 Drawing Sheets

(56) References Cited

OTHER PUBLICATIONS

Medicinenet—Citocoline ("MedicineNet") was published at https://www.medicinenet.com/citicoline/supplements-vitamins.htm by at least Jul. 28, 2016.
Tianna Red, distributed by We Care Distributor Inc., alleged by Defendant MRSS to have been on sale or otherwise available to the public at least as early as Jul. 1, 2017.
Tianna Green distributed by We Care Distributor Inc., alleged by Defendant MRSS to have been on sale or otherwise available to the public at least as early as Jul. 1, 2017.
Tianna Gold, distributed by We Care Distributor Inc., alleged by Defendant MRSS to have been on sale or otherwise available to the public at least as early as Jul. 1, 2017.
Saatcioglu et al., "A Case of tianeptine abuse," Spring 2006, Abstract, pubmed.ncbi.nlm.nih.gov/16528638/.
Kisa et al., "Is it possible to be dependent to Tianeptine, an antidepressant? A case report," Apr. 13, 2007, Abstract, pubmed.ncbi.nlm.nih.gov/17270334/.
Transparency Committee, "STABLON 12.5 mg, coated tablet," Dec. 5, 2012, Haute Autorite De Sante.
Bence et al., "Neonatal Abstinence Syndrome Following Tianeptine Dependence During Pregnancy," Jan. 2016, Abstract, pediatrics.aappublications.org/content/137/1/e20151414.
Lee et al., "Effects of tianeptine on symptoms of fibromyalgia via BDNF signaling in a fibromyalgia animal model," Jun. 26, 2017, Korean J Physiol Pharmacol.
McCarthy et al., "eye on excipients," May 2017, Tablets & Capsules, CSC Publishing.
Gurun et al., "The Effect of Peripherally Administered CDP-Choline in an Acute Inflammatory Pain Model: The role of alpha-7 Nicotinic Acetylcholine Receptor," 2009, Anesthesia & Analgesia vol. 108, No. 5.
Kanat et al., "Preclinical evidence for the antihyperalgesic activity of CDP-choline in oxaliplatin-induced neuropathic pain," 2013, Journal of the Balkan Union of Oncology.
Roohi-Azizi et al., "Citicoline Combination Therapy for Major Depressive Disorder: A Randomized, Double-Blind, Placebo-Controlled Trial," Clinical Neuropharmacology vol. 40, No. 1, Jan./Feb. 2017.
Brown et al., "A randomized, double-blind, placebo-controlled trial of citicoline for bipolar and unipolar depression and methamphetamine dependence," Dec. 20, 2012, Journal of Affective Disorders.
Mossad & J Distribution's Reply in Support of Its Motion to Dismiss Karmagreen, LLC's Claims for Contributory Infringement, Induced Infringement, and Willful Infringement, and M&J's Response in Opposition to Karmagreen's Alternative Motion for Leave to Amend the Complaint; *Karmagreen, LLC v. Mossad & J Distribution Inc, A/K/A M& J Distribution*, United States District Court Northern District of Georgia, Case No. 1:20-cv-03968; Dec. 14, 2020.
Complaint for Patent Infringement; *Karmagreen, LLC v. MRSS Inc*, United States District Court Northern District of Georgia, Case No. 1:20-cv-00674; Feb. 16, 2021.
Brief in Support of Motion to Dismiss Karmagreen, LLC's Claims for Contributory Infringement, Induced Infringement, and Willful Infringement; *Karmagreen, LLC v. Mossad & J Distribution Inc, A/K/A M & J Distribution*, United States District Court Northern District of Georgia, Case No. 1:20-cv-03968; Nov. 2, 2020.
Complaint for Patent Infringement; *Karmagreen, LLC v. Mossad & J Distribution Inc, A/K/A M& J Distribution*, United States District Court Northern District of Georgia, Case No. 1:20-cv-03968; Sep. 25, 2020.

* cited by examiner

DIETARY SUPPLEMENT

RELATED DOCUMENTS

This document is related to, incorporates by reference in its entirety, and claims the priority benefit of U.S. patent application Ser. No. 15/672,013 filed Aug. 8, 2017 by James Peter Morrissette.

FIELD OF THE INVENTION

The present invention relates to dietary supplements.

SUMMARY OF THE INVENTION

It is an object of the present invention to provide a dietary supplement.

It is another object of the present invention to provide a dietary supplement for absorption by a human or animal with the supplement containing at least two ingredients that provide at least one desired effect or benefit.

In an exemplary embodiment of the present invention, a dietary supplement can comprise a first ingredient of sakae naa; and a second ingredient of kava.

In another exemplary embodiment, the dietary supplement can further comprise a third ingredient of stearate and/or a fourth ingredient of silicate.

In still another exemplary embodiment, a total weight of the dietary supplement can be made up of about 3-15% of tianeptine sodium, about 60-85% sakae naa, about 0.5-3% stearate, and about 5-28% silicate.

In a further exemplary aspect, the total weight of the dietary supplement can be made up of about 4.46% of tianeptine sodium, about 74.04% sakae naa, about 1.5% stearate, and about 20% silicate.

In another exemplary embodiment, the first ingredient can include tianeptine sodium and tianeptine free acid.

In still a further exemplary aspect, a total weight of the dietary supplement can be made up of about 1-14% of tianeptine sodium, about 1-14% of tianeptine free acid, about 40-85% sakae naa, about 0.5-3% stearate, and about 5-28% silicate.

In yet another exemplary aspect, the total weight of the dietary supplement can be made up of about 2.23% of tianeptine sodium, about 8.93% of tianeptine free acid, about 67.35% sakae naa, about 1.5% stearate, and about 20% silicate.

In a further exemplary embodiment, the dietary supplement can further consists essentially of a third ingredient of kava.

In yet a further exemplary aspect, a total weight of the dietary supplement can be made up of about 1-14% of tianeptine sodium, about 1-14% of tianeptine free acid, about 8-18% kava, about 40-65% sakae naa, about 0.5-3% stearate, and about 5-28% silicate.

In still yet a further exemplary aspect, the total weight of the dietary supplement can be made up of about 2.23% of tianeptine sodium, about 8.93% of tianeptine free acid, about 13.39% kava, about 53.95% sakae naa, about 1.5% stearate, and about 20% silicate.

In another exemplary embodiment, a dietary supplement can consist essentially of a first ingredient of tianeptine, a second ingredient of cytidine diphosphate-choline (hereinafter "CDP choline" or "CDP"), and a third ingredient of alpha glycerylphosphorylcholine (hereinafter "Alpha GPC" or "GPC").

In a further exemplary aspect, the first ingredient can include at least one of tianeptine sodium and tianeptine free acid.

In another exemplary aspect, a total weight of the dietary supplement can be made up of about 1-14% of tianeptine sodium, about 1-14% of tianeptine free acid, about 20-34% CDP Choline, about 30-60% Alpha GPC, about 0.5-3% stearate, and about 5-28% silicate. In yet another exemplary aspect, a total weight of the dietary supplement can be made up of about 2.23% of tianeptine sodium, about 8.93% of tianeptine free acid, about 27.04% CDP Choline, about 45% Alpha GPC, about 1.5% stearate, and about 15.3% silicate.

In further exemplary embodiments, the present invention further includes methods of forming a dietary supplement, comprising steps of: creating a composition of matter comprising any combination of ingredients described herein, and filling a container, such as a capsule, for example and not in limitation, with the composition of matter to form the dietary supplement.

These and other exemplary aspects and embodiments of the present invention are further described herein.

DETAILED DESCRIPTION

Figure 1:
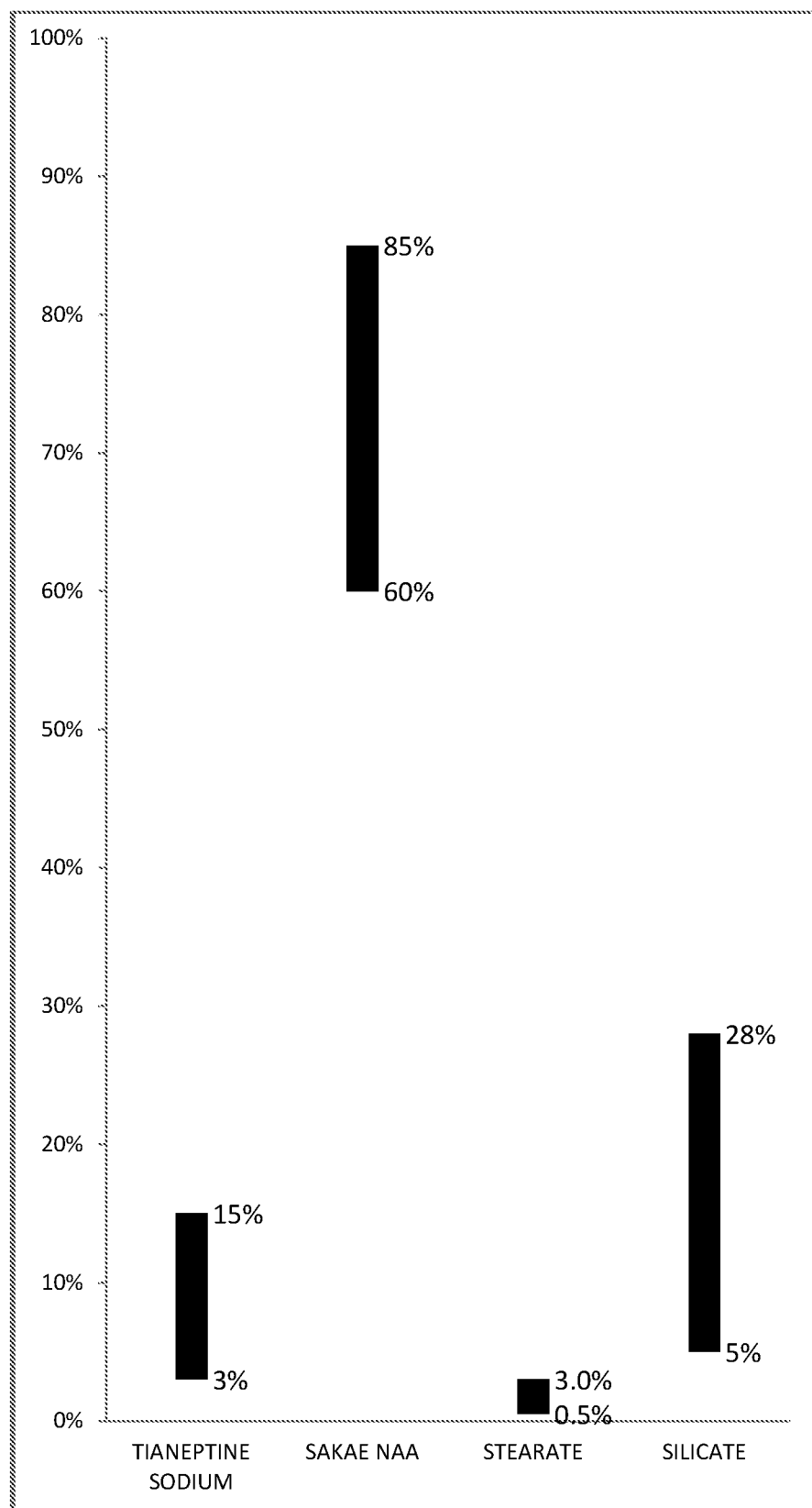
FIG. 1 illustrates an exemplary combination of ingredients of a dietary supplement.

It should be noted that this disclosure includes a plurality of embodiments, with a plurality of ingredients, elements, and aspects, and such ingredients, elements, and aspects need not necessarily be interpreted as being conjunctively required by one or more embodiments of the present invention. Rather, all combinations of the one or more ingredients, elements, and/or aspects can enable a separate embodiment of the present invention, which may be claimed with particularity in this or any one or more future filed Non-Provisional patent applications. Moreover, any particular ingredients, proportions, amounts, or ranges disclosed herein, whether expressly or implicitly, are to be construed strictly as illustrative and enabling, and not necessarily limiting. Therefore, it is expressly set forth that such ingredients, proportions, amounts, and/or ranges independently or in any combination of one of more thereof, are merely illustratively representative of one or more embodiments of the present invention and are not to be construed as necessary in a strict sense.

Further, to the extent the same ingredient, element, or aspect is defined differently within this or any related disclosure, whether expressly or implicitly, the broader definition is to take absolute precedence, with the distinctions encompassed by the narrower definition to be strictly construed as optional.

Illustratively, perceived benefits of the present invention can include functional utility, including the provisioning of any vitamin, mineral, medicine, dietary substance, or desired effect-causing substance, whether expressly or implicitly stated herein, or apparent herefrom. However, it is expressly set forth that these benefits are not intended as exclusive. Therefore, any explicit, implicit, apparent, or synergistic benefit from the disclosure herein is expressly deemed as applicable to the present invention.

According to the present invention, a dietary supplement can be provided in any type of capsule, pill, or liquid form, or any other desired form that is ingestible, including absorbable through non-oral means, by an organism, such as a human or other mammal. Further, according to the present invention, ingredients herein can initially be provided in powder or liquid form, with or without subsequent processing.

According to exemplary embodiments of the present invention, a dietary supplement can include any combination of one or more of the following active ingredients: Tianeptine; Sakae Naa; Kava; cytidine diphosphate-choline; and Alpha-glycerophosphocholine.

In an exemplary aspect, Tianeptine is tricyclic antidepressant, has both antidepressant and anxiolytic properties, and has been used in medical treatment regiments for depression, anxiety, asthma, and irritable bowel syndrome. Further, Tianeptine may provide anticonvulsant (anti-seizure) and analgesic (painkilling) activities, and may also beneficially effect cognition with those having depression-induced cognitive dysfunction. Though considered a tricyclic antidepressant, tianeptine can exhibit different pharmacological properties than typical tricyclic antidepressants based on research suggestions that it produces antidepressant results through an indirect alteration of glutamate receptor activity and a release of brain-derived neurotrophic factor ("BDNF"), which can affect neural plasticity.

Tianeptine can be provided in various salt forms, such as Tianeptine Sodium and Tianeptine Sulfate, to produce increased or desired bioavailability, absorption, and overall effectiveness. Anecdotal evidence suggests that Tianeptine Sulfate may be more effective and possess a longer duration than the Tianeptine Sodium. While Tianeptine Sulfate may not necessarily be more potent than Tianeptine Sodium, it is believed that it is metabolized more slowly by the human body, which can allow for single daily doses. Moreover, as Tianeptine Sulfate is metabolized more slowly, there may be less potential for addiction. Further, Tianeptine Sulfate appears to provide more sustained effects, as compared to Tianeptine Sodium, which tends to provide a peak effect in its antidepressant benefit with its effects suddenly ending.

Tianeptone can also be provided as Tianeptine Free Acid, which is not hygroscopic (cf., salt forms of Tianeptine, supra), and therefore, not as adversely affected by humidity exposure for short periods of time as salt forms. Tianeptine Free Acid further includes the following particular aspects relative to Tianeptine Salt: its absorption rate tends to be more gradual over a longer time period without an undesired "drop off" effect; its taste and odor tend to be more desirable; it is partially water soluble, and highly soluble in sodium hydroxide, potassium hydroxide, ethanol and ether; and it can be converted to Tianeptine Sodium Salt relatively easily.

Sakae Naa (or Combretum Quadrangulare) is an ingredient derived from leaves of the Combretum Quadrangulare tree. Sakae Naa extract has been used as an herbal medicine for common colds, sore throats, and mild pain relief, and has also been found to have both anti-bacterial and anti-inflammatory properties. Sakae Naa can provide energizing, stimulating, mood-lifting, and mildly sedating effects that can last up to four hours. Notably, Sakae Naa has been avoided where relaxation alone is desired.

Kava is a root found on South Pacific islands, and has been used by Islanders for medicinal and ceremonial purposes. Kava can provide a calming effect by modifying brain waves similar to those from calming medicines, such as diazepam, and can relieve anxiety, restlessness, sleeplessness, stress symptoms, and pain. Kava has also been used to prevent convulsions and as a muscle relaxer. Kava can be prepared as a liquid (as a tea, for example), or in powder or tincture forms.

CDP Choline is an intermediate in the generation of phosphatidylcholine from choline, a common biochemical process in cell membranes, and naturally occurs in cells of human and animal tissue as well as in organs. CDP Choline has been used to benefit memory function and behavior in those with cognitive deficits, and has been approved for treatment of head trauma, stroke, and neurodegenerative disease in both Japan and Europe. Further, CDP Choline may be beneficial following an ischemic stroke, and has been suggested to improve visual functionality in patients with glaucoma.

Alpha GPC is a cholinergic compound that can be used for promoting cognitive abilities and enhancing athletic output. It also has been used to support cellular membranes, and may additionally assist in preventing cognitive declination.

In an exemplary aspect of the present invention, a dietary supplement can optionally include non-essential ingredients, such as magnesium or vegetable stearate ("stearate") and calcium silicate (silicate), for example and not in limitation. Stearate can be provided as an anti-adherent, as its lubricating properties can reduce or prevent ingredients from adhering to equipment during processing of ingredients; whereas silicate can be provided as an anti-caking agent, which can maintain the free-flowing properties of powdered ingredients of the present invention during manufacturing thereof.

As illustrated in FIG. 1, according to an exemplary embodiment of the present invention, a dietary supplement can consist essentially of a first ingredient of Tianeptine Sodium; and a second ingredient of Sakae Naa. In exemplary aspects, Tianeptine Sodium and Sakae Naa can be provided in a powdered or generally dry form (such as a powder, for example and not in limitation); and the Tianeptine Sodium can have about a 98-99% purity and the Sakae Naa can be about a 10 to 1 extract. As further illustrated in FIG. 1, the Tianeptine can be between about 3 and 15% of the total weight (such as milligrams, for example and not in limitation) of the dietary supplement, and the Sakae Naa can be between about 60 and 85% of the total weight. Further, such a supplement can optionally include between about 0.5 and 3.0% Stearate and/or about 5 and 28% Silicate of the total weight. For example and not in limitation, a dietary supplement can be about 4.46% Tianeptine Sodium, about 74.04% Sakae Naa, about 1.5% Stearate, and about 20% Silicate.

Figure 2:
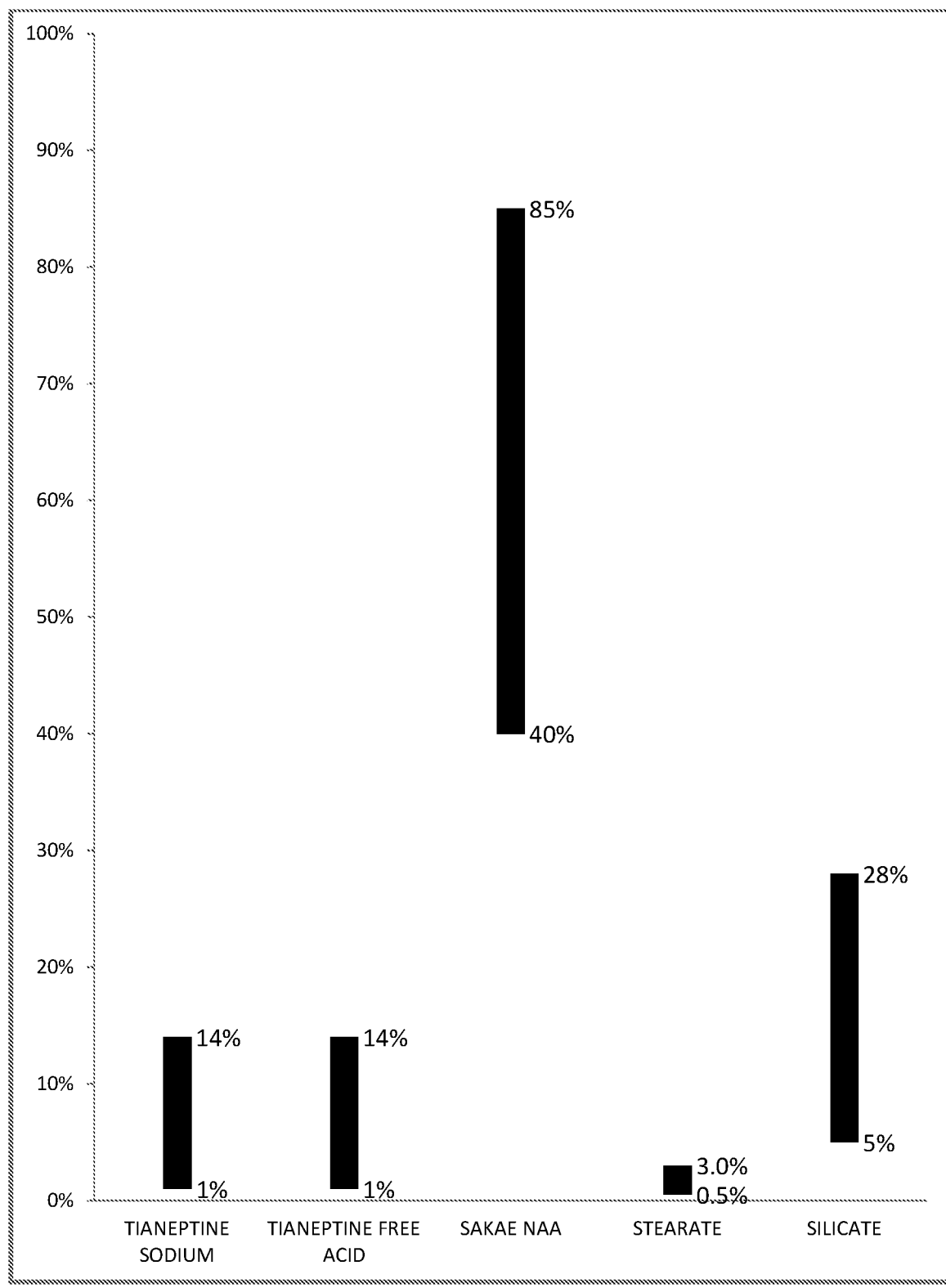
FIG. 2 illustrates another exemplary combination of ingredients of a dietary supplement.

As illustrated in FIG. 2, according to another exemplary embodiment of the present invention, a dietary supplement can consist essentially of a first ingredient of Tianeptine Sodium; a second ingredient of Tianeptine Free Acid; and a third ingredient of Sakae Naa. In exemplary aspects, Tianeptine Sodium, Tianeptine Free Acid, and Sakae Naa can be provided in a powdered or generally dry form (such as a powder, for example and not in limitation); and the Tianeptine Sodium and Free Acid can have about 98-99% purities and the Sakae Naa can be about a 10 to 1 extract. As further illustrated in FIG. 2, the Tianeptine Sodium and Free Acid can each be between about 1 and 14% of the total weight (such as milligrams, for example and not in limitation) of the dietary supplement, and the Sakae Naa can be between about 40 and 85% of the total weight. Further, such a supplement can optionally include between about 0.5 and 3.0% Stearate and/or about 5 and 28% Silicate of the total weight. For example and not in limitation, a dietary supplement can be about 2.23% Tianeptine Sodium, about 8.93 Tianeptine Free Acid, about 67.35% Sakae Naa, about 1.5% Stearate, and about 20% Silicate.

Figure 3:
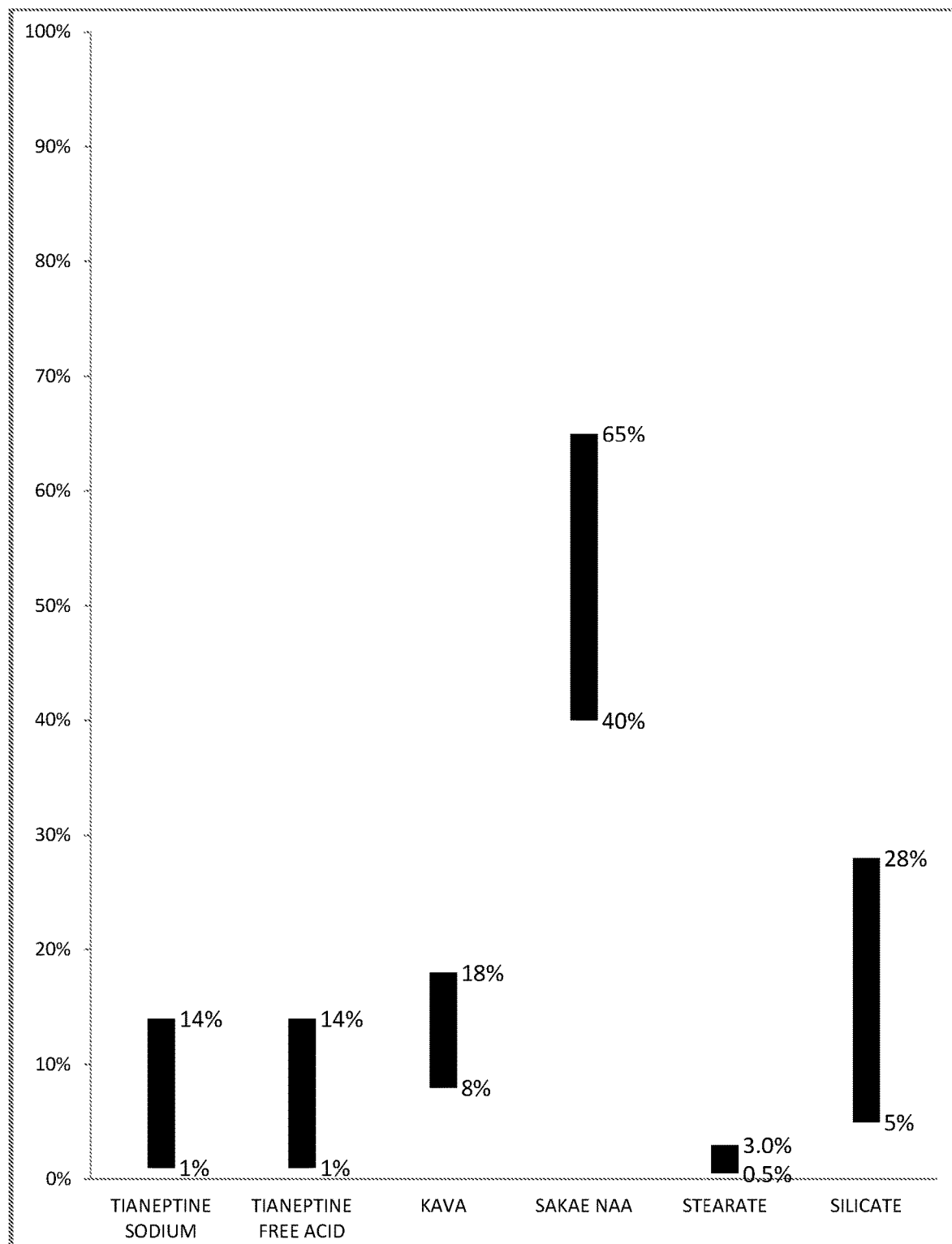
FIG. 3 illustrates a further exemplary combination of ingredients of a dietary supplement.

As illustrated in FIG. 3, according to yet another exemplary embodiment of the present invention, a dietary supplement can consist essentially of a first ingredient of Tianeptine Sodium; a second ingredient of Tianeptine Free Acid; a third ingredient of Kava; and a fourth ingredient of Sakae Naa. In exemplary aspects, Tianeptine Sodium, Tianeptine Free Acid, Kava, and Sakae Naa can be provided in a powdered or generally dry form (such as a powder, for example and not in limitation); and the Tianeptine Sodium and Free Acid can have about 98-99% purities, the Kava can be provided as about a 70% extract, and the Sakae Naa can be about a 10 to 1 extract. As further illustrated in FIG. 3, the Tianeptine Sodium and Free Acid can each be between about 1 and 14% of the total weight (such as milligrams, for example and not in limitation) of the dietary supplement, the Kava can be between about 8 and 18% of the total weight, and the Sakae Naa can be between about 40 and 65% of the total weight. Further, such a supplement can optionally include between about 0.5 and 3.0% Stearate and/or about 5 and 28% Silicate. For example and not in limitation, a dietary supplement can be about 2.23% Tianeptine Sodium, about 8.93 Tianeptine Free Acid, about 13.39% Kava, about 53.95% Sakae Naa, about 1.5% Stearate, and about 20% Silicate.

Figure 4:
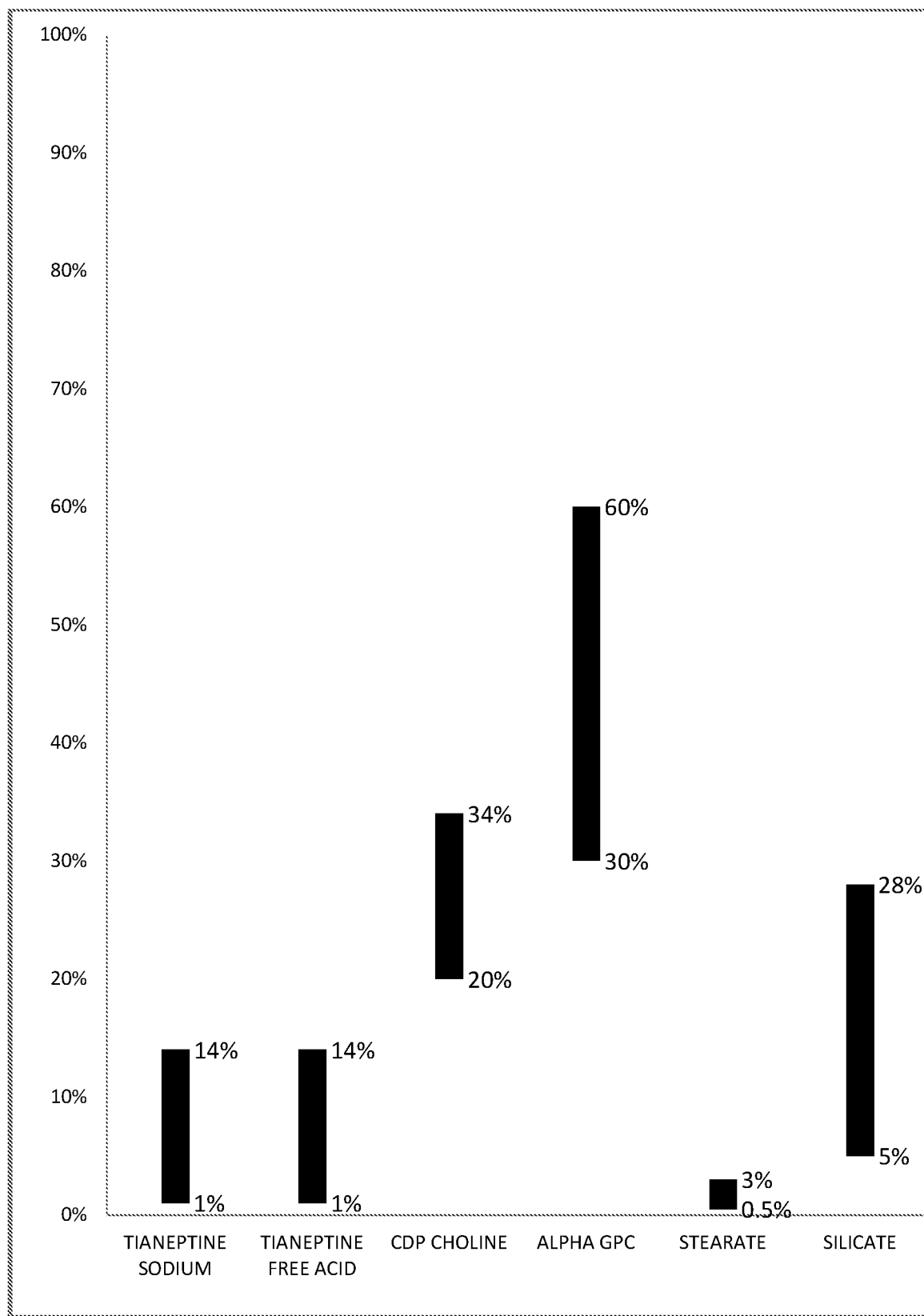
FIG. 4 illustrates yet another exemplary combination of ingredients of a dietary supplement.

As illustrated in FIG. 4, according to yet another exemplary embodiment of the present invention, a dietary supplement can consist essentially of a first ingredient of Tianeptine Sodium; a second ingredient of Tianeptine Free Acid; a third ingredient of CDP Choline; and a fourth ingredient of Alpha GPC. In exemplary aspects, the Tianeptine Sodium, Tianeptine Free Acid, CDP Choline, and Alpha GPC can be provided in a powdered or generally dry form (such as a powder, for example and not in limitation); and the Tianeptine Sodium and Free Acid can have 98-99% purities, the CDP Choline with about a 98-99% purity, and the Alpha GPC can be about 60% purity. As further illustrated in FIG. 4, the Tianeptine Sodium and Free Acid can each be between about 1 and 14% of the total weight (such as milligrams, for example and not in limitation) of the dietary supplement, the CDP Choline can be between about 20 and 34% of the total weight, and the Alpha GPC can be between about 30 and 60% of the total weight. Further, such a supplement can optionally include between about 0.5 and 3.0% Stearate and/or about 5 and 28% Silicate. For example and not in limitation, a dietary supplement can be about 2.23% Tianeptine Sodium, about 8.93 Tianeptine Free Acid, about 27.04% CDP Choline, about 45% Alpha GPC, about 1.5% Stearate, and about 15.3% Silicate.

In additional exemplary embodiments, the present invention includes methods of forming a dietary supplement, comprising steps of: creating a composition of matter comprising any combination of ingredients described above; and providing the composition of matter in one of a liquid and solid form as the dietary supplement.

Figure 5:
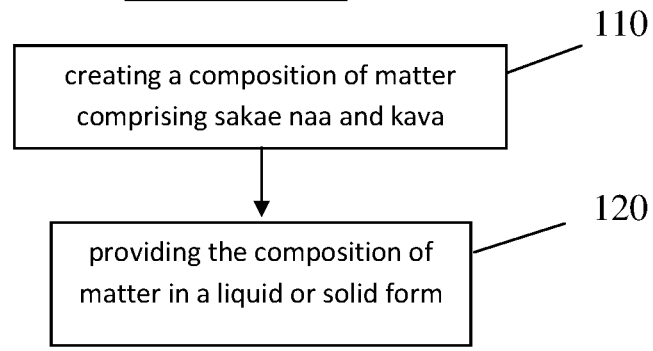
FIG. 5 illustrates an exemplary method of forming a dietary supplement including a step of creating a composition of matter, and a step of providing the composition of matter in a liquid or solid form.
Figure 6:
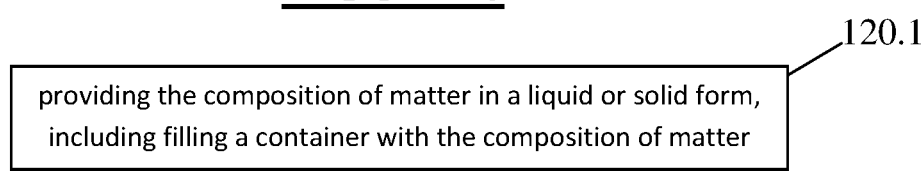
FIG. 6 illustrates an exemplary method step of providing the composition of matter, which includes filling a container with the composition of matter.
Figure 7:
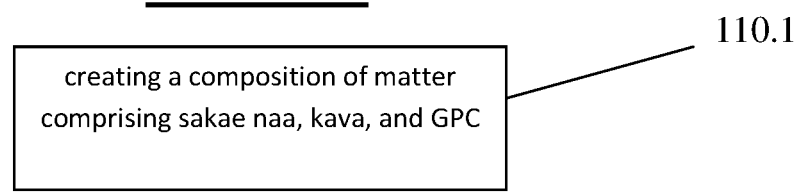
FIG. 7 illustrates an exemplary method step of creating a composition of matter comprising sakae naa and kava, in which the composition of matter can optionally further comprise GPC.

FIG. 5 illustrates an exemplary method of forming a dietary supplement comprising steps of creating a composition of matter comprising sakae naa and kava (step 110); and providing the composition of matter in a liquid or solid form as the dietary supplement (step 120). FIG. 6 illustrates another exemplary step of providing a composition of matter, so as to additionally include filling a container with the composition of matter (step 120.1); whilst FIG. 7 illustrates another exemplary step of creating a composition of matter comprising sakae naa, kava, and optionally GPC (step 110.1).

It will be apparent to one of ordinary skill in the art that the manner of making and using the claimed invention has been adequately disclosed in the above-written description of the exemplary embodiments and aspects.

It should be understood, however, that the invention is not necessarily limited to the specific embodiments, aspects, arrangement, and components shown and described above, but may be susceptible to numerous variations within the scope of the invention. For example and not in limitation, optional ingredients of stearate and silicate are merely illustrative, and equivalent ingredients to achieve the same functionality thereof are available. Therefore, the specification and drawings are to be regarded in an illustrative and enabling, rather than a restrictive, sense.

Accordingly, it will be understood that the above description of the embodiments of the present invention are susceptible to various modifications, changes, and adaptations, and the same are intended to be comprehended within the meaning and range of equivalents of the appended claims.

Therefore, I claim:

1. A method of forming a dietary supplement, comprising steps of:
   creating a composition of matter comprising a first ingredient of sakae naa and a second ingredient of kava; and
   providing the composition of matter in one of a liquid and a solid form as the dietary supplement.

2. The method of claim 1, wherein providing the composition of matter includes filling a container with the composition of matter.

3. The method of claim 1, wherein the composition of matter further comprises at least one of a third ingredient of stearate and a fourth ingredient of silicate.

4. The method of claim 3, wherein providing the composition of matter includes filling a container with the composition of matter.

5. The method of claim 1, wherein the composition of matter further comprises a third ingredient of stearate and a fourth ingredient of silicate.

6. The method of claim 5, wherein providing the composition of matter includes filling a container with the composition of matter.

* * * * *